United States Patent [19]

Lukase et al.

[11] Patent Number: 5,122,058
[45] Date of Patent: * Jun. 16, 1992

[54] FORCEPS WITH INSERTS FOR REMOVING PREMOLAR AND ANTERIOR DENTAL CROWNS

[75] Inventors: Stephen P. Lukase, Glendale, Ariz.; Thomas A. Lukase, 2670 Greentree La., La Jolla, Calif. 92037

[73] Assignee: Thomas A. Lukase, Glendale, Ariz.

[*] Notice: The portion of the term of this patent subsequent to Sep. 3, 2008 has been disclaimed.

[21] Appl. No.: 601,669

[22] Filed: Oct. 23, 1990

[51] Int. Cl.$^5$ ............................................. A61C 3/14
[52] U.S. Cl. ............................................. 433/159
[58] Field of Search ............................ 433/159, 160

[56] References Cited

U.S. PATENT DOCUMENTS

| | | | |
|---|---|---|---|
| 831,307 | 9/1906 | Spahn | 433/160 |
| 1,636,861 | 7/1927 | Griveau | 433/159 |
| 2,674,800 | 4/1954 | Osborn et al. | 433/159 |
| 3,834,026 | 9/1974 | Klein | 433/159 |
| 3,898,738 | 8/1975 | Linden | 433/159 |
| 4,197,647 | 4/1980 | Goldenth | 433/159 |

Primary Examiner—John J. Wilson
Attorney, Agent, or Firm—Cahill, Sutton & Thomas

[57] ABSTRACT

A pair of dental forceps, whether configured for anterior or premolar teeth, includes a pair of jaw mounted removable cushioning and gripping inserts for conformingly gripping and frictionally retaining a respective crown to be removed without imposing stress concentrations sufficient to mar or damage the crown.

16 Claims, 2 Drawing Sheets

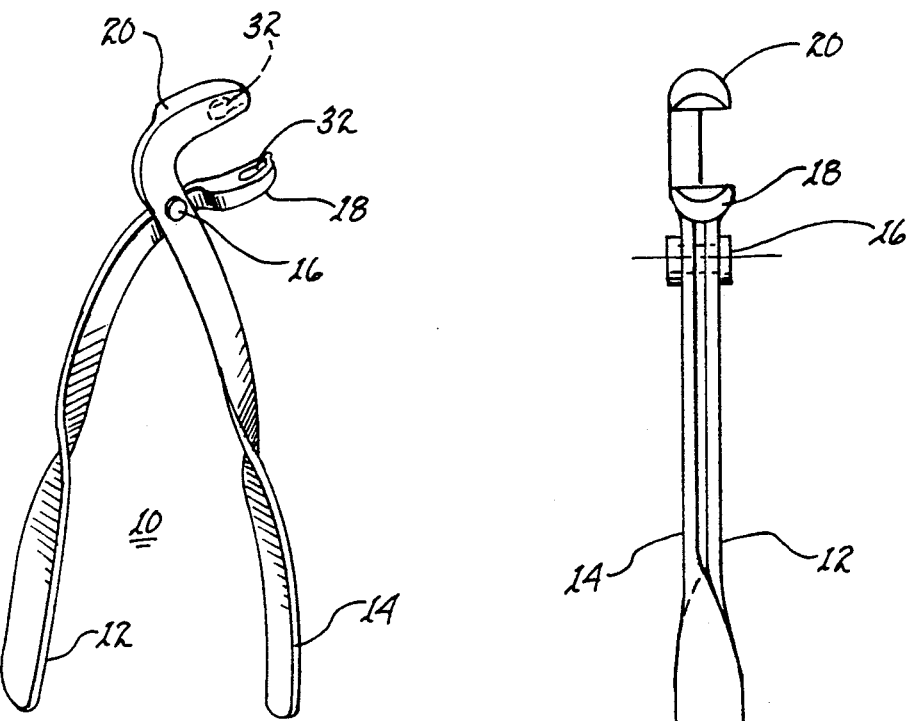
fig. 1
fig. 2
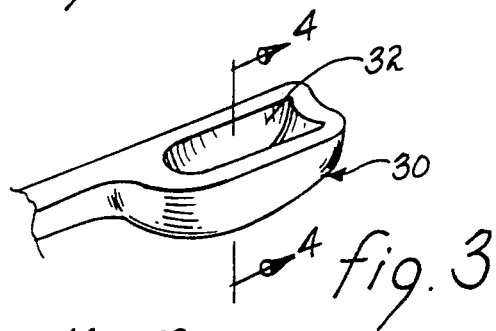
fig. 3
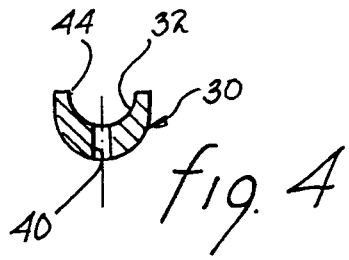
fig. 4
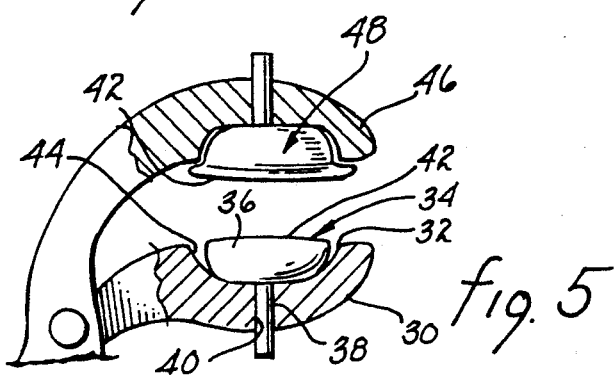
fig. 5
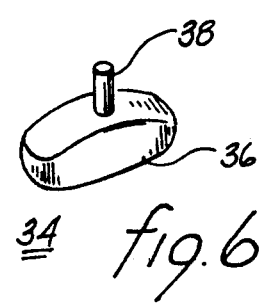
fig. 6

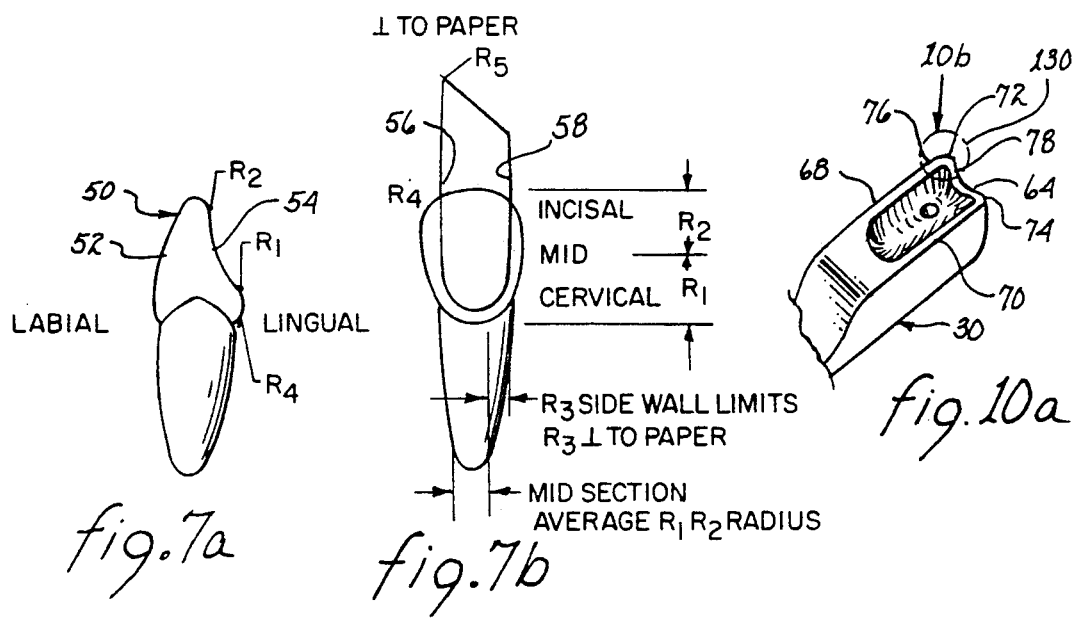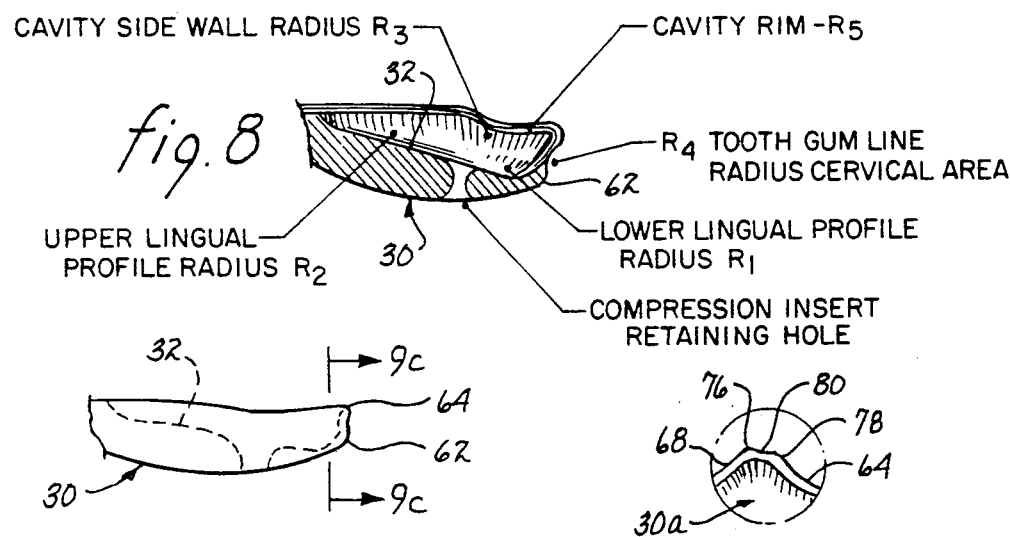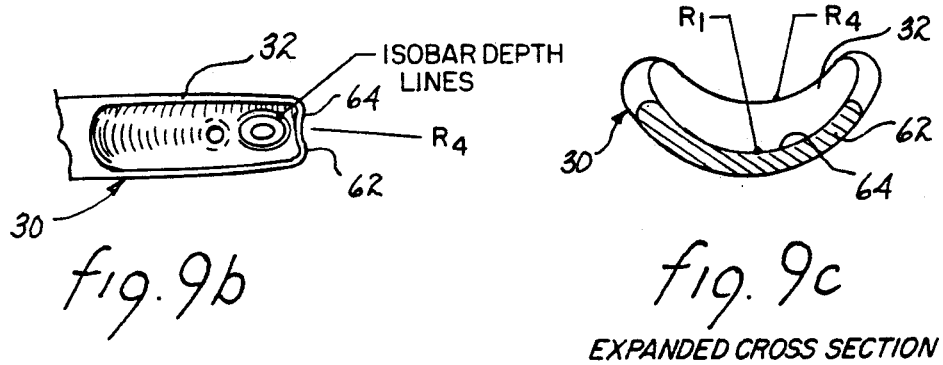

FORCEPS WITH INSERTS FOR REMOVING PREMOLAR AND ANTERIOR DENTAL CROWNS

BACKGROUND OF THE INVENTION

1. Field of the Invention

The present invention relates to dental implements and, more particularly, to forceps for removing dental prosthetic devices.

2. Description of the Prior Art

Dental forceps, particularly configured for use upon the anterior, premolar or molar teeth have been available for years for purposes of extracting a tooth. These forceps have jaws particularly angled and of a length to facilitate grasping a particular tooth. During tooth extraction, it is very important that a firm grip of the tooth be achieved and it is of no consequence if the enamel of the tooth cracks or if the tooth is otherwise damaged.

The forceps used for extracting teeth have been developed over a period of many decades to provide an effective combination of gripping a tooth and ease of manipulation of the gripped tooth to effect the extraction process. Primarily, the developmental work has been directed to the length and angulation of the gripping jaws To remove a crown for purposes of reattaching it more securely to develop a better seal or for adjustment purposes, it is very important that the crown not be aesthetically damaged or physically distorted. To use a conventional pair of extraction forceps for this purpose presents a real problem for the following reasons. The jaws of the forceps may damage the surface of the crown even though a good firm grip is established. If the forceps are only lightly squeezed to avoid damage to the crown, the jaws may slip from the crown and cause injury to the patient or damage to other teeth or restorations. For these reasons, many dentists use their fingers, and particularly their fingernails, to grasp the cervical ridge of the crown to dislodge and extract the crown. Since not all dentists have sufficient power in their fingers for this purpose, crown removal is a problem. Similarly, not all dentists have sufficiently robust fingernails to withstand the forces imposed without bending and causing substantial pain to the dentist. A potential problem of fungal infection also exists.

Various devices have been developed over the years to attempt to solve the above enumerated problems. In the 1920s, a clamp forceps was developed which cooperated with a detachably attached rubber dam to minimize damage to a crown while retaining sufficient gripping and extracting force. Regrettably, this device was difficult and awkward to use as a practical matter. Some time later, a pair of forceps was developed which included a pair of opposed curved surfaces lined with resilient material for gripping a crown. These forceps were very difficult to use for all teeth due to the different requirements of grip and manipulation imposed by the placement of each tooth within the mouth.

A yet further device was developed which is of a plier like configuration having one jaw of the pair of jaws oriented to contact and bear against the proximal edge of the crown while the second jaw was penetrably inserted through a passageway cut in the top of the crown to bear against the underlying tooth. In situations where the underlying tooth is little more than a post, this device is ineffective. Moreover, the requirement for a passageway through the cusp of the crown necessitated repair and reconstruction of the crown prior to remounting.

SUMMARY OF THE INVENTION

A pair of extraction forceps, configured in correspondence with the tooth supporting a crown to be removed includes removable inserts disposed in the jaws for gripping with sufficient force to permit removal of the crown while preventing damage or disfigurement to the crown surface and structure. The replaceabilty of the inserts permits autoclaving or other sterilizing procedures of the forceps and the inserts may be disposable after one use. Moreover, the forceps with inserts are readily useable for extracting bridges and other dental prosthetic devices which may need adjustment, repair or reconstruction without causing damage during such extraction.

It is therefore a primary object of the present invention to provide a pair of forceps for grasping and removing a dental prosthetic device without damaging it.

Another object of the present invention is to provide an extraction tool for extracting premolar and anterior crowns.

Still another object of the present invention is to provide resilient conformable inserts for the jaws of a pair of forceps to grasp and remove a crown.

A further object of the present invention is to provide removable inserts for use with dental forceps to extract dental prosthetic devices.

A still further object of the present invention is to provide a method for extracting a dental prosthetic device without damaging the device during extraction.

A yet further object of the present invention is to provide a method for firmly grasping but not damaging a dental crown to be removed.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 illustrates a perspective view of a pair of forceps;

FIG. 2 illustrates a side view of the forceps shown in FIG. 1;

FIG. 3 illustrates a jaw of the forceps shown in FIGS. 1 and 2;

FIG. 4 is a cross sectional view taken along lines 44, as shown in FIG. 3;

FIG. 5 is a partial cross sectional view of the jaws of the forceps shown in FIG. 1;

FIG. 6 illustrates a removable insert;

FIGS. 7a and 7b illustrate representative side and rear elevational views of premolar and anterior crowns mounted upon a tooth;

FIG. 8 illustrates a cross sectional view of a forceps jaw;

FIGS. 9a, 9b and 9c illustrate cross sectional, top and end views of the jaw segment illustrated in FIG. 8; and FIGS. 10a and 10b illustrate modifications to the jaw for accommodating cervical ridge anomalies.

DESCRIPTION OF THE PREFERRED EMBODIMENT

To assist a dentist in extracting teeth, numerous extraction forceps have been developed for groups of teeth which represent similar or related accessibility, direction of extraction and manipulation impediments. These forceps can generally be categorized as being suitable for anterior, premolar or molar teeth. It is to be understood that further gradations also exist. As shown in plan view in FIG. 1, a pair of forceps 10, which forceps are of a configuration generally used for premolar and anterior teeth. The pair of forceps includes handles 12, 14 pivotally attached to one another by pivot means 16. Jaws 18, 20 associated with handles 12, 14, respectively, extend generally perpendicular to the respective handles. The degree of bend of jaws 18, 20 with respect to handles 12, 14 primarily dictates the type of tooth with which the pair of forceps is to be used.

For tooth extraction purposes, jaws 18, 20 are of surgical steel or similar material which permits a very firm rigid grip of a tooth to be extracted. Various composite plastic materials can also be used. Whether the act of gripping and manipulating the tooth during extraction results in damage to the tooth enamel or the structure of the tooth is generally not of significance.

When a crown is to be removed in the event the seal for the crown has been compromised or the crown needs to be repaired or adjusted, it is important to prevent damage to the crown during the act of removal. Were such damage to occur, reconstruction or replacement of the crown would result in substantial expense which should be avoided. Because of the fragility of crowns, a dentist often must rely upon the strength of his fingers to effect removal since implements for this purpose and which have a low probability of causing damage to the crown do not exist. All dentists do not have sufficient strength in their fingers to effect removal of a crown. Furthermore, the space or volume available within the oral cavity to manually grip a crown may be a limiting factor of the ease with which a crown can be removed by manual manipulation.

Since dental forceps have been developed to facilitate the grasp of any of a patient's teeth, and as a crown usually has the same dimensions and configuration as the formerly existing complete tooth, the modification of a pair of forceps intended for extraction of such tooth would vastly ease removal of the crown.

Referring to FIGS. 3 and 4, there is illustrated a jaw 30, which may be commensurate with one of jaws 18, 20, formed with a depression 32 disposed in the working surface of the jaw. As shown in FIGS. 5 and 6, an insert 34 includes a body portion 36 configured to mate with and be received within depression 32. To assist in removably installing the insert, a tang 38 may extend rearwardly. This tang is penetrably insertable into passageway 40 to protrude therefrom. Upon grasping the protruding tang, insert 34 can be pulled, as well as pushed, into seated engagement with depression 32. Face 42 of the insert serves as the working surface for gripping contact with the crown to be extracted. The face of one or both of the inserts may extend peripherally beyond perimeter 44 of depression 32, as shown in FIG. 5. The extended part of the insert would rest upon and be supported by the surface of jaw 30 surrounding perimeter 44. Preferably, face 42 of the insert is displaced from the adjacent surface of jaw 30. Such displacement of the face will tend to preclude physical contact between jaw 30 and the crown to be removed whereby damage to the crown due to pressure exerted by the hard surface of jaw 30 would be precluded.

Jaw 46 and insert 48 are in opposed relationship to but correspond with jaw 30 and insert 34 in structure and function.

Inserts 34 and 48 can be relatively easily removed from the respective supporting jaw by simply grasping the insert body and pulling the insert out of the respective depression. Thereafter, the pair of forceps may be autoclaved or otherwise sterilized without concern for damage to the insert. The pair of inserts usable with each pair of jaws may be rendered sterile by conventional techniques and packaged accordingly prior to use. It is contemplated that each pair of inserts would be disposable.

Preferably, inserts 34 and 48 are of resilient flexible material, such as a rubber composition or a plastic composition, which is suitable for molding or other fabrication. Sufficient resistance to compressibility must be present to prevent the pressures exerted by pair of jaws 30, 46 from coming into contact with the crown to be removed. Furthermore, the inserts must exert sufficient friction upon the surface of the crown to prevent slippage without the application of sufficient compressive forces which might collapse or otherwise damage the crown upon disengagement from the underlying supporting tooth.

The configuration of each of jaws 30, 46 and inserts 34, 48 is preferably commensurate with the surface of the crown to be grasped by the respective jaw/insert, i.e. the jaw cavity corresponds to the basic lingual/labial impression of the surfaces to be engaged. Such correspondence will tend to distribute uniform forces along the contacted crown surface (both vertically and horizontally) to minimize the likelihood of damage or deformation to the crown surface. Moreover, a greater effective gripping area of essentially uniformly applied forces will result and extraction of the crown will be eased.

A representative tooth mounted premolar and anterior crown 50 is illustrated in FIGS. 7a and 7b. Outward surface 52 is generally referred to as the labial surface while inward surface 54 is referred to as the lingual surface. These are the two surfaces contacted by the jaws of forceps during extraction. Furthermore, it is generally 60% of these surfaces which is gripped. This portion of the lingual surface is identified by lines 56, 58 (the cavity rim associated with radius R5 (FIG. 8)). To promote and ensure a non slipping grip, the forceps jaws preferably conform with the various curvatures depicted by designations R1, R2, R3, R4 and R5 in the cervical, mid and incisal portions of the crown.

FIG. 8 illustrates a cross section of a typical depression 32 (see also FIGS. 3 and 5) formed in a jaw 30. The depression illustrated is representative of the curvature of the lingual surface 54; it is understood that the curvature of the depression used in conjunction with labial surface 52 would be commensurately configured. More particularly, the curvature or radius at each of locations R1, R2, R3, R4 and R5 would be specifically contoured to the mating curvature of the crown. That is, R1 would be equivalent with the lower lingual profile, R2 would be equivalent to the upper lingual profile, R3 would be equivalent to the cavity sidewall, R4 would be equivalent to the tooth gum line in the cervical area and R5 would be equivalent to the curvature of the rim of the depression commensurate with the contact area of the lingual surface extending longitudinally along the tooth generally proximate lines 56, 58 (see FIG. 7b).

Referring jointly to FIGS. 9a, 9b and 9c, further views of depression 32 in jaw 30 are illustrated. Terminal end 62 includes a curved edge 64 conforming in general to the curvature attendant R1 of crown 50. The remaining curvatures and contours of depression 32 generally conform with that of the mid third section of the lingual surface of crown 50.

The insert to be fitted within the jaw and its depression depicted in FIG. 8 and in FIGS. 9a, 9b and 9c will compressingly conform with the depression to receive the commensurate lingual or labial surface of a crown and exert uniform forces thereagainst upon gripping of the crown by the forceps. Such uniformity of gripping forces will reduce stress concentrations to minimize damage or deformation to the crown and minimize the likelihood of slipping while providing a high degree of control for manipulation of the crown during extraction.

FIGS. 10a and 10b partially illustrate a variant 30a of jaw 30 for accommodating anomalies of the dental prosthetic to be removed. In jaw 30, edges 68, 70 join with terminal edge 64 at locations which define relatively sharp points 72, 74. Depending upon the structure and configuration of both the tooth and the associated dental prosthetic, there may be anomalies in the area of the cervical ridge and primarily in the mesio/distal length. The presence of sharp points 72, 74 on jaw 30 may create difficulties in effecting facile gripping and removal of the dental prosthetic. To eliminate such cause for difficulty, variant jaw 30a may be used in the area of one of the pair of sharp points (72) identified within circle 130 in FIG. 10a, segments of edges 68, 64 extending from the junction to locations identified by 76, 78 are removed. The resulting edge, identified by numeral 80 in FIG. 10b, eliminates point 72 preset in jaw 30. A similar modification is performed on edges 70, 64 forming point 74 to replace this point with an edge equivalent to edge 80. Such modification to jaw 30 will not negatively affect the efficacy of edge 64 in engaging the cervical ridge of the dental prosthetic as a functional equivalent of a dentist's fingernail and it will accommodate the aforementioned possible anomalies.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A pair of forceps for gripping in a non damaging manner a dental prosthetic device to effect removal of the dental prosthetic device, said pair of forceps comprising in combination:
   a) a pair of handles for manipulating said pair of forceps;
   b) a pair of jaws for gripping opposed sides of the dental prosthetic, one end of each handles of said pair of handles including one jaw of said pair of jaws disposed at one end;
   c) means for pivotally interconnecting said pair of handles to relocate said pair of jaws toward and away from one another in response to pivotal movement of said handles relative to one another, said pair of jaws being located and movable within a plane defined by the pivotal movement of said pair of handles;
   d) at least one jaw of said pair of jaws including a cavity and a perimeter defining said cavity, said perimeter including an indented edge segment for engaging the cervical ridge of the dental prosthetic device, each said cavity being in opposed facing relationship to the other jaw of said pair of jaws, each said cavity including a surface defined by said perimeter which is three dimensionally compatible with the corresponding surface of the dental prosthetic device to be gripped; and
   e) an insert demountably mountable within each of said cavities for contacting the dental prosthetic device and for restraining contact between the dental prosthetic device and the respective one of said perimeters.

2. The apparatus as set forth in claim 1 wherein each of said inserts is of resilient flexible material.

3. The apparatus as set forth in claim 1 wherein each of said inserts is sufficiently compressible to conform with the surface of the dental prosthetic device in contact with the insert while exerting essentially uniform forces across the surface contacted.

4. The apparatus as set forth in claim 1 wherein at least one of said inserts extends beyond said perimeter of the respective one of said cavities.

5. The apparatus as set forth in claim 4 wherein each of said inserts extend beyond said perimeter of the respective one of said cavities.

6. The apparatus as set forth in claim 1 wherein at least one of said cavities includes a passageway extending through the respective one of said jaws.

7. The apparatus as set forth in claim 6 wherein at least one of said inserts includes a tang for penetrable engagement with said passageway.

8. The apparatus as set forth in claim 7 wherein each of said cavities includes said passageway and wherein each of said inserts includes said tang.

9. The apparatus as set forth in claim 1 wherein each of said cavities is elongated in the direction of the longitudinal axis of the respective one of said jaws.

10. The apparatus as set forth in claim 1 wherein the longitudinal axis of each jaw of said pair of jaws is generally normal to the longitudinal axis of the respective one of said pair of handles.

11. The apparatus as set forth in claim 1 including means disposed upon each jaw of said pair of jaws for contacting the dental prosthetic device and for restraining contact between the dental prosthetic device and each jaw of said pair of jaws.

12. The apparatus as set forth in claim 1 wherein each jaw of said pair of jaws includes one of said cavities and said perimeter defining each of said cavities.

13. A method for griping with a pair of forceps in a non damaging manner a dental prosthetic device to effect removal of the dental prosthetic device, said method comprising in combination:
   a) manipulating the pair of handles of the pair of forceps;
   b) gripping opposed sides of the dental prosthetic with a pair of jaws extending from the pair of handles in response to manipulation of the handles;
   c) contacting the dental prosthetic with a resilient insert disposed in a cavity formed in at least one jaw of the pair of jaws while simultaneously restraining contact between the dental prosthetic and that position of the jaw extending from the perimeter of the respective one of the cavities; and d) exerting essentially uniform forces across the area of contact of the labial and lingual surfaces of the dental prosthetic device by forming the cavity in each jaw in correspondence with the labial and lingual surface to be received.

14. A pair of forceps for gripping within a plane defined by the pivotal movement of said pair of forceps and in a non damaging manner a dental prosthetic device having a cervical ridge to effect removal of the dental prosthetic device, said pair of forceps including a pair of handles supporting jaws for gripping opposed labial and lingual surfaces of the dental prosthetic device, said pair of forceps comprising in combination:
   a) a first cavity formed in one jaw of the pair of jaws and generally conforming with one of the labial and lingual surfaces of the dental prosthetic device to be removed;
   b) a second cavity formed in the other jaw of the pair of jaws and generally conforming in configuration with the other of the labial and lingual surfaces of the dental prosthetic device to be removed, said second cavity being oriented in opposing relationship to said first cavity;
   c) a first perimeter for defining the edge of said first cavity, said first perimeter including an inwardly curved edge segment for engaging a section of the cervical ridge of the dental prosthetic device;
   d) a second perimeter for defining the edge of said second cavity, said second perimeter including a further inwardly curved edge segment for engaging a further section of the cervical ridge of the dental prosthetic device;
   e) first and second inserts disposed within said first and second cavities, respectively, for bearing against the corresponding labial and lingual surfaces to grip the dental prosthetic and effect removal of the dental prosthetic device upon manipulation of said pair of forceps.

15. The apparatus as set forth in claim 14 wherein said first and second inserts are of resilient material.

16. The apparatus as set forth in claim 14 including means for removably securing said first and second inserts within the respective first and second cavities.

* * * * *